United States Patent [19]

Burkinshaw

[11] Patent Number: 5,064,427
[45] Date of Patent: Nov. 12, 1991

[54] APPARATUS FOR INSERTING AND WITHDRAWING HUMERAL PROSTHESIS

[75] Inventor: Brian D. Burkinshaw, Pflugerville, Tex.

[73] Assignee: Intermedics Orthopedics, Inc., Austin, Tex.

[21] Appl. No.: 700,530

[22] Filed: May 14, 1991

[51] Int. Cl.⁵ .............................. A61F 2/00; A61F 2/40; A61B 17/56
[52] U.S. Cl. ............................................. 606/99; 623/18; 623/19
[58] Field of Search ..................... 623/19, 18, 22, 23; 606/86–88, 89, 99, 100

[56] References Cited

U.S. PATENT DOCUMENTS

| | | | |
|---|---|---|---|
| 3,818,514 | 6/1974 | Clark | 606/86 X |
| 3,857,389 | 12/1974 | Amstutz | 606/86 |
| 4,222,382 | 9/1980 | Antonsson et al. | 606/100 |
| 4,642,121 | 2/1987 | Keller | 623/18 |
| 4,964,865 | 10/1990 | Burkhead et al. | 623/19 |

FOREIGN PATENT DOCUMENTS 2615097 11/1988 France .............................. 606/99

*Primary Examiner*—Ronald Frinks
*Attorney, Agent, or Firm*—John R. Merkling

[57] ABSTRACT

An apparatus for inserting and withdrawing a prosthesis into and out of the humerus comprising a sleeve and taper protector which fit over a neck on the humeral prosthesis. A shaft delivers the force of an impact hammer to the prosthesis to drive the prosthesis into the bone. The prosthesis is locked into the sleeve by a pivoting arm which has tabs which permit prosthesis to be withdrawn from the humerus. An orthogonal handle and bolt serve both to tighten the pivot arm against the prosthesis and to provide accurate angular orientation for implanting the prosthesis.

6 Claims, 2 Drawing Sheets

APPARATUS FOR INSERTING AND WITHDRAWING HUMERAL PROSTHESIS

FIELD OF MY INVENTION

My invention relates to apparatus for inserting orthopedic prostheses into bone and, in particular, to an apparatus for inserting a humeral prosthesis into the humerus, or upper arm bone.

BACKGROUND OF MY INVENTION

The glenoid cavity is located on the upper external boarder of the scapula between the acromion process and the coracoid, a bony formation know as the scapula head. The glenoid cavity is a shallow, pear-shaped articular surface whose longest diameter is from above downward and whose direction is outward and forward from the body. It is broader below than above, and at its apex there is a slight depression, the supra-glenoid tubercle, to which is attached is the long tendon of the biceps muscle. The cavity is covered with cartilage and its margins, slightly raised, give attachment to a fibrocartilaginous structure, the glenoid ligament, by which the cavity is deepened.

The glenoid cavity articulates with a large, rounded head at the proximal end of the humerus, or upper arm bone. The head is nearly hemispherical in form and is directed upward, inward, and a little backward. Its surface is smooth and coated with cartilage.

By process of aging or disease, the glenoid cavity or the head of the humerus or both may degrade and it may be necessary to replace these natural structures with prostheses. Both glenoid and humeral prostheses are known. An exemplary structure is described in U.S. Pat. No. 4,964,865 Burkhead, Dale, and myself, which patent is assigned to the same assignee as my present invention. The patent also describes other glenoid/humeral prostheses which are presently available.

It is difficult to implant a glenoid or humeral prostheses accurately because of the constrained geometry of the shoulder joint. An incision exposing the joint should be as small as possible and trauma in manipulating the joint should be minimized. At the same time it is necessary to implant a humeral prosthesis accurately and firmly in the humerus so that integration of the prosthesis will integrate with the humeral bone, the prosthesis will not work its way out of the bone, and the articulating surfaces of the prosthesis will mate accurately with a glenoid or a glenoid prosthesis. It is sometimes necessary, also, to withdraw a humeral prosthesis out of the humerus.

With the foregoing in mind, it has been an object of my invention to provide any apparatus which attaches to a humeral prosthesis for implantation of the prosthesis into the humerus.

Another object of my invention is to provide an apparatus which can transmit the forces necessary for implanting a prosthesis without deforming that prosthesis.

It is also an object of my invention to provide an apparatus which makes it easy to control the angle of presentation of humeral prosthesis into the bone.

Another important object of my invention is to provide an apparatus which can withdraw a humeral prosthesis out of the humerus.

SUMMARY OF MY INVENTION

I have invented an apparatus for inserting and withdrawing a prosthesis into and out of the humerus comprising a sleeve and taper protector which fit over a neck on the humeral prosthesis. A shaft delivers the force of an impact hammer to the prosthesis to drive the prosthesis into the bone. The prosthesis is locked into the sleeve by a pivoting arm which has tabs which permit prosthesis to be withdrawn from the humerus. An orthogonal handle and bolt serve both to tighten the pivot arm against the prosthesis and to provide accurate angular orientation for implanting the prosthesis.

These and other objects and features of my invention will become apparent to those skilled in the art from the following detailed description, made with reference to the accompanying drawings.

DETAILED DESCRIPTION OF MY PREFERRED EMBODIMENT

Figure 1:
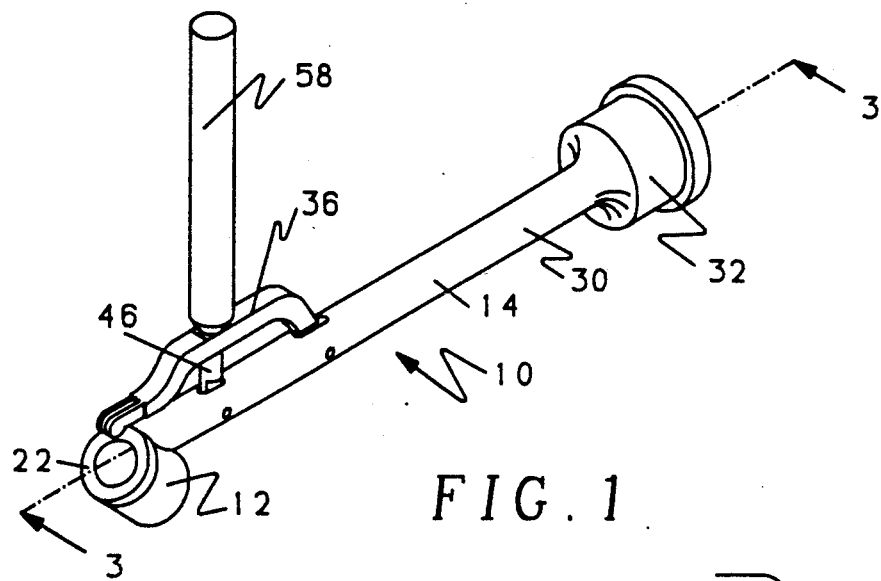
FIG. 1 is a perspective view of an apparatus according to my invention.
Figure 2:
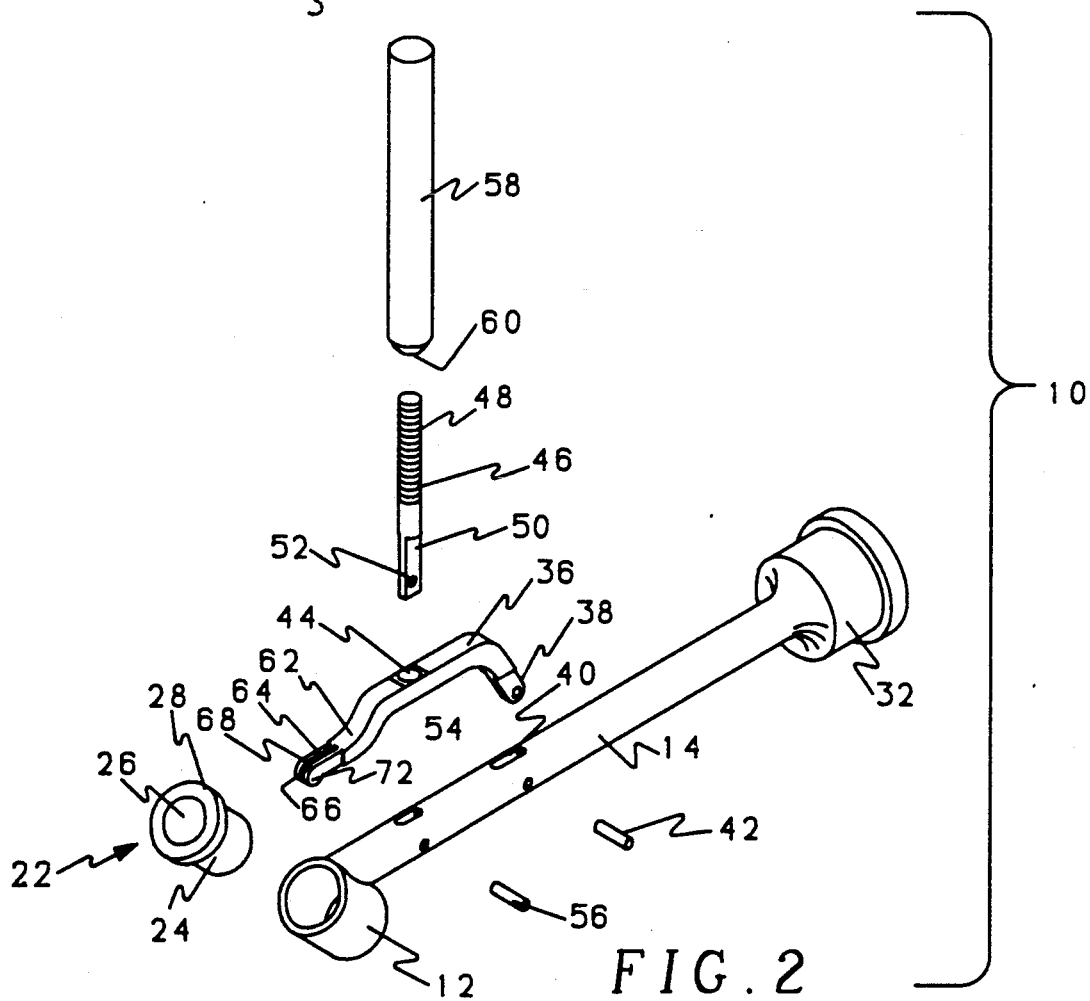
FIG. 2 is an exploded view of the apparatus of FIG. 1.

I will now describe my preferred embodiment by reference to the accompanying drawings. Like numerals refer to like parts thereout. Referring particularly to FIG. 1, I have shown an apparatus, generally designated 10, for inserting and withdrawing a humeral prosthesis into and out of a humerus. The apparatus comprises an inclined sleeve 12 attached to a shaft. The axis of the shaft and the axis of the sleeve 12 form an acute angle, as seen most clearly in FIG. 3. This permits the shaft 14 to be aligned with a stem 16 of a humeral prosthesis 18 while the sleeve 12 engages a neck 20 on the humeral prosthesis.

A taper protector 22 slides into the sleeve so that the apparatus can be sized to receive various diameters of prosthesis necks. The taper protector is preferably formed of a non-metallic substance, such as acetyl copolymer. The other parts of my apparatus are preferably metallic. The taper protector comprises a cylinder 24 with a central bore 26. A circumferential lip 28 prevents the taper protector from being pushed through the sleeve 12.

Figure 3:
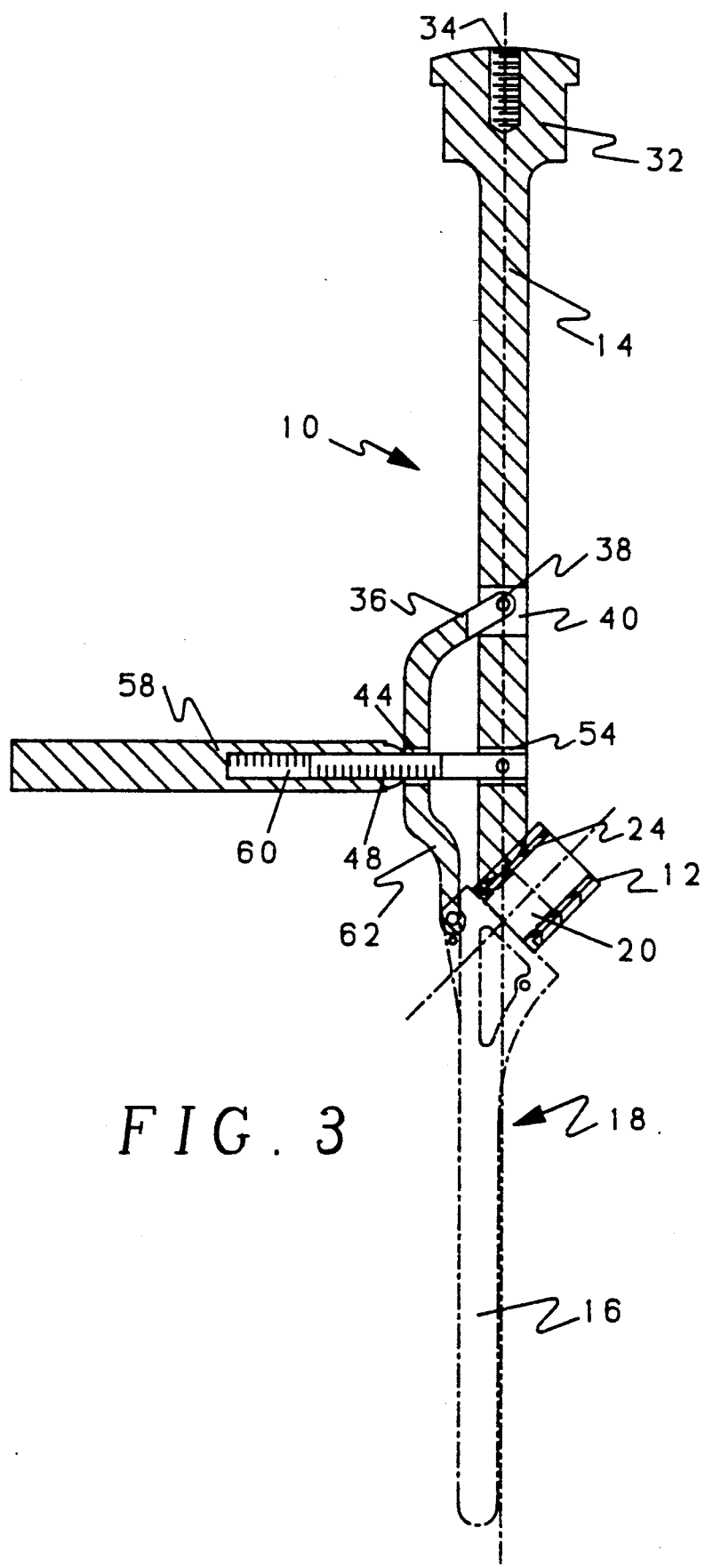
FIG. 3 is a through section of the apparatus of FIG. 1 taken along line 3—3 with a component of a humeral prosthesis shown in phantom lines.

At a proximal end 30 of the shaft 14 there is an impact head 32. The impact head 32 can be of any suitable design for receiving blows from a conventional impact hammer to drive the humeral prosthesis into the humerus. As can be seen in FIG. 3, the alignment of the shaft and the humeral prosthesis is such that force of blows against the impact head will be carried directly along the shaft 16 of the prosthesis. A threaded bore 34 may be provided in the impact head so that a conventional impact hammer can be screwed into the head. This permits reverse blows to be delivered to the apparatus 10 to withdraw the prosthesis 18 out of the humerus.

To lock the prosthesis into the sleeve and taper protector, I have provided a pivot arm 36. The pivot arm 36 comprises a pivot 38 which swivels in a slot 40 in the shaft 14. A pin 42 holds the pivot in the slot 40. midway along the pivot arm, I have provided a through bore 44 through which is inserted a pivot bolt 46. The pivot bolt has a threaded end 48 and a flattened end 50 with a through bore 52. The flattened end 50 fits into a slot 54 in the shaft 14 and a pin 56 fastens the pivot bolt within the shaft. An orthogonal handle 58 with a threaded interior bore 60 screws onto the pivot bolt 46. Tightening the handle 58 onto the pivot bolt clamps the pivot arm against the prosthesis 18, giving it a positive lock. In addition, since the handle 58 is orthogonal to the shaft 14, the angular orientation of the prosthesis can be accurately controlled as the prosthesis is driven into the humerus.

As described above, tightening the handle 58 presses a distal end 62 of the pivot arm 36 against the prosthesis 18. To further lock the prosthesis, I have provided two parallel stabilizers 64, 66 at the distal end 62. These stabilizers define a central slot 68 which fits over a fin 70 on the humeral prosthesis. This minimizes rocking of the prosthesis within the apparatus. In addition, each of the stabilizers 64, 66 has a distal tab 72 which fits into a recess 74 in the humeral prosthesis. These tabs aid in withdrawing the prosthesis and take some of the load which would otherwise be carried in torque by the pivot arm and in tension by the taper protector and sleeve.

When the humeral prosthesis 18 is placed into the apparatus 10 according to my invention, the prosthesis can be driven into the humerus accurately and securely. Both the orientation of the prosthesis stem and its angular displacement can be controlled. Moreover, the force necessary for implanting the prosthesis can be delivered to the prosthesis without damage to the prosthesis or the prosthesis neck. After the prosthesis has been implanted, the handle 58 can be loosened, thus disengaging the pivot arm. The apparatus can be simply removed from the prosthesis and a prosthetic ball surface can be placed on the neck, as is known in the art.

My invention may be embodied in other specific forms without departing from the spirit or essential characteristics thereof. The foregoing description, therefore, is considered in all respects to be illustrative and not restrictive, the scope of my invention being defined by the appended claims. All changes which come within the meaning of equivalency of the claims are therefor intended to be encompassed therein.

I claim as my invention:

1. An apparatus for inserting and withdrawing a humeral prosthesis from a humerus, the apparatus comprising
    a shaft for transmitting forces to the prosthesis;
    a sleeve mounted on a distal end of said shaft, said sleeve having a central bore oriented at an acute angle with respect to said shaft for receiving a neck of said prosthesis; and
    pivoting arm means pivotally connected to said shaft for clamping against said prosthesis.

2. The apparatus according to claim 1 further comprising means for tightening said pivoting arm means against said prosthesis.

3. The apparatus according to claim 2 wherein the tightening means comprise a pivot bolt connected to said shaft and passing through said pivot arm and a handle threadedly connected to said pivot bolt.

4. The apparatus according to claim 3 wherein the pivot arm further comprises at least one tab adjacent said prosthesis for engaging a recess in said prosthesis.

5. The apparatus according to claim 4 wherein the pivot arm comprises stabilizer means defining a slot for engaging a fin on said prosthesis.

6. The apparatus according to claim 5 further comprising neck protector means received within said sleeve for protecting said neck of said prosthesis.

* * * * *